US011534515B2

(12) United States Patent
Charles et al.

(10) Patent No.: US 11,534,515 B2
(45) Date of Patent: Dec. 27, 2022

(54) SANITIZATION DEVICE AND ADAPTOR FOR USE WITH THE SAME

(71) Applicant: SOCLEAN, INC., Peterborough, NH (US)

(72) Inventors: Robert A. Charles, New Boston, NH (US); Keith Jon Jorgenson, Stoughton, MA (US)

(73) Assignee: SOCLEAN INC., Peterborough, NH (US)

( * ) Notice: Subject to any disclaimer, the term of this patent is extended or adjusted under 35 U.S.C. 154(b) by 0 days.

(21) Appl. No.: 17/228,898

(22) Filed: Apr. 13, 2021

(65) Prior Publication Data

US 2021/0322608 A1    Oct. 21, 2021

Related U.S. Application Data

(60) Provisional application No. 63/010,297, filed on Apr. 15, 2020.

(51) Int. Cl.
*A61L 2/20* (2006.01)
*A61L 2/26* (2006.01)

(52) U.S. Cl.
CPC .............. *A61L 2/202* (2013.01); *A61L 2/26* (2013.01); *A61L 2202/11* (2013.01); *A61L 2202/122* (2013.01); *A61L 2202/123* (2013.01); *A61L 2202/15* (2013.01); *A61L 2202/24* (2013.01); *A61L 2202/26* (2013.01)

(58) Field of Classification Search
CPC ........ A61L 2/202; A61L 2/26; A61L 2202/26; A61L 2202/24; A61L 2202/122; A61L 2202/15; A61L 2202/123; A61L 2202/11
See application file for complete search history.

(56) References Cited

U.S. PATENT DOCUMENTS

| 9,358,316 B2* | 6/2016 | Leyva | A61M 16/1095 |
| 2015/0314340 A1* | 11/2015 | Falk | B08B 3/04 134/36 |
| 2016/0235875 A1* | 8/2016 | Schmidt | A61L 2/26 |
| 2018/0140730 A1* | 5/2018 | Leyva | A61L 2/202 |
| 2020/0222568 A1* | 7/2020 | Lucio | A61L 2/26 |

FOREIGN PATENT DOCUMENTS

| DE | 20007705 | * | 8/2000 | A61L 2/18 |

OTHER PUBLICATIONS

English translation of DE20007705 (Year: 2000).*

* cited by examiner

*Primary Examiner* — Regina M Yoo
(74) *Attorney, Agent, or Firm* — Grossman, Tucker, Perreault & Pfleger, PLLC

(57) ABSTRACT

A sanitization device may include an ozone operating system configured to generate ozone, a sanitization compartment, a distribution line fluidly coupling the ozone operating system to the sanitization compartment, and an adaptor disposed within the sanitization compartment. The adaptor may be configured to couple to a mask and may be further configured to be fluidly coupled to the distribution line such that ozone passes through the adaptor and into the sanitization compartment.

11 Claims, 11 Drawing Sheets

SANITIZATION DEVICE AND ADAPTOR FOR USE WITH THE SAME

TECHNICAL FIELD

The present disclosure is generally directed to sanitization devices and more specifically to a sanitization device configured to sanitize a device (or article) using a sanitization fluid (e.g., ozone gas) that is incident on one or more surfaces of the device.

BACKGROUND INFORMATION

Devices (e.g., medical devices, such as a mask, consumer devices, such as a mobile phone or one or more keys, and etc.) are exposed to numerous environments in which harmful bacteria and/or viruses can come into contact with and reside on the devices. Without proper sanitization, further use of these devices after exposure can result in the spread of harmful bacteria and/or viruses. Accordingly, before reuse, devices may be sanitized in order to reduce the risk of spreading harmful bacteria and viruses.

One example of a medical device is a mask (e.g., a continuous positive airway pressure mask, a respirator mask, and/or any other type of mask). Masks are worn on a user's face and come into direct contact bodily fluids exhaled from a user's mouth and/or nose. These fluids may include harmful bacteria and/or viruses. In some instances, a mask may be designed to collect harmful bacteria and/or viruses such that a user of the mask does not inhale harmful bacteria and/or viruses present within an environment. Accordingly, reuse of a mask, without proper sanitization, may increase a risk of spreading harmful bacteria and/or viruses to others as well as the user.

BRIEF DESCRIPTION OF THE DRAWINGS

These and other features advantages will be better understood by reading the following detailed description, taken together with the drawings wherein.

DETAILED DESCRIPTION

The present disclosure is generally directed to a sanitization device configured to sanitize a device. The sanitization device includes a sanitization compartment configured to receive a device (e.g., a medical device such as a mask), a sanitizing fluid operating system configured to generate a sanitizing fluid (e.g., ozone gas), a distribution line to deliver the sanitizing fluid to the sanitization compartment, and an adaptor configured to position a device disposed thereon within a flow path of the sanitizing fluid flowing within the sanitization compartment.

Although the technologies described herein can be used with many sanitizing fluids, the present disclosure focuses on the use of ozone as a sanitizing gas. This is because ozone ($O_3$) gas is an effective sanitizer yet is relatively safe for consumer use. Because of its strong oxidizing properties, ozone can effectively kill or otherwise remove a wide range of organic and inorganic contaminants such as yeasts, bacteria, molds, viruses, other pathogens, and/or pollutants with which it comes into contact, e.g., via oxidation. Naturally over time and/or as it oxidizes contaminants, ozone is chemically reduced to oxygen ($O_2$), which is safe for human consumption and for release into the environment. Ozone is also relatively easy to generate on site (and thus does not require the use of a storage tank), and leaves little or no chemical residue. For those and other reasons, ozone has been identified as a safe and effective sanitizing gas for use in the present disclosure. It should be understood, however, that the technologies described herein are not limited to the use of ozone and may be employed with a wide variety of sanitizing fluids.

Figure 1:
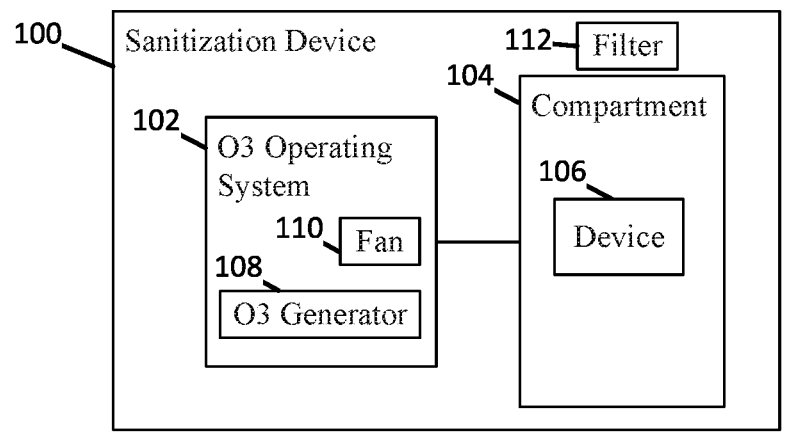
FIG. 1 shows a schematic block diagram of an example of a sanitization device, consistent with embodiments of the present disclosure.

FIG. 1 shows a schematic block diagram of a sanitization device 100. As shown, the sanitization device 100 includes an ozone operating system 102 and a sanitization compartment 104. The ozone operating system 102 is configured to generate ozone and is fluidly coupled to the sanitization compartment 104. The sanitization compartment 104 is configured to receive a device (or article) to be sanitized 106 (e.g., a medical device, such as a mask, a consumer device, such as a mobile phone or wallet, and/or any other device) therein. In operation, ozone is generated by the ozone operating system 102 and caused to flow into the sanitization compartment 104. Once in the sanitization compartment 104, the ozone comes into contact with the device 106, sanitizing the device 106. Before being exhausted from the sanitization compartment 104, the ozone may be caused to be broken down into oxygen (e.g., by passing the ozone through a filter 112).

In some instances, the ozone operating system 102 includes an ozone generator 108 and a fan 110. The ozone generator 108 generates ozone and the fan 110 urges the ozone to flow into the sanitization compartment 104. In some instances, the ozone operating system 102 may be external to the sanitization compartment 104. In this instance, the ozone operating system 102 may be fluidly coupled to the sanitization compartment 104 through a distribution line. In other instances, the ozone operating system 102 is disposed within the sanitization compartment 104 such that ozone generated is dispersed directly into the sanitization compartment 104 from the ozone operating system 102.

Figure 2:
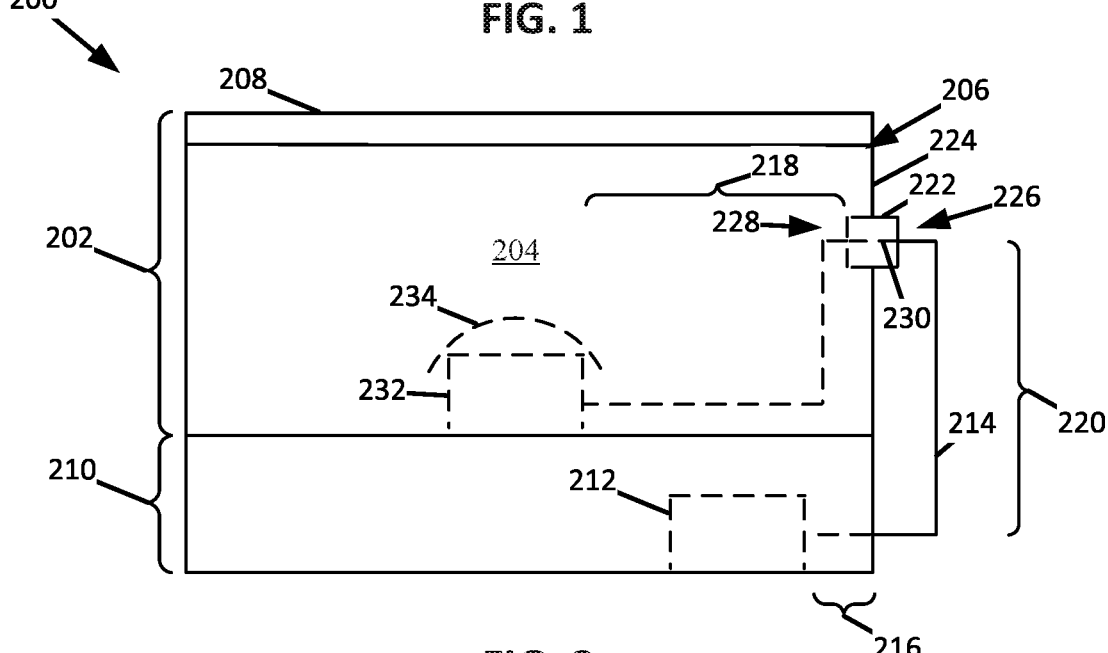
FIG. 2 shows a schematic side view of a sanitization device, which may be an example of the sanitization device of FIG. 1, consistent with embodiments of the present disclosure.

FIG. 2 shows a schematic view of an example of a sanitization device 200, which may be an example of the sanitization device 100 of FIG. 1. As shown, the sanitization device 200 includes a sanitization compartment 202 defining a sanitization cavity 204 having at least one open end 206, and a lid 208 extending over the open end 206 and configured to selectively enclose the sanitization cavity 204. The sanitization device 200 further includes a hardware compartment 210 for receiving an ozone operating system 212 configured to generate ozone gas to be delivered to the sanitization cavity 204.

As shown, a distribution line 214 fluidly couples the ozone operating system 212 to the sanitization compartment 202. As such, the ozone gas generated by the ozone operating system 212 is delivered to the sanitization compartment 202 through the distribution line 214. The distribution line 214 includes a hardware portion 216 extending within the hardware compartment 210, a sanitization portion 218 extending within the sanitization compartment 202, and a connecting portion 220 extending between the hardware portion 216 and the sanitization portion 218. The distribution line 214 may include one or more tubes, wherein each tube corresponds to at least one of the hardware portion 216, the sanitization portion 218, and/or the connecting portion 220 of the distribution line 214. The example, the hardware portion 216 and the connecting portion 220 of the distribution line 214 may be a first continuous tube and the sanitization portion 218 may be a second continuous tube, wherein the first continuous tube is different from the second continuous tube. By way of further example, the distribution line 214 may be one continuous tube that defines each the hardware portion 216, the sanitization portion 218, and the connecting portion 220.

The sanitization device 200 may also include a connector 222 that extends through a sidewall 224 of the sanitization compartment 202. In some instances, the connector 222 may be integrally formed from the sidewall 224 of the sanitization compartment 202. At least one end surface of the connector 222 may be substantially coplanar with a surface of the sidewall 224 (e.g., a surface of the sidewall 224 defining the sanitization cavity 204). A first connection end 226 of the connector 222 is configured to couple to the connecting portion 220 of the distribution line 214. A second connection end 228 of the connector 222 is configured to couple to the sanitization portion 218 of the distribution line 214. A fluid channel 230 extends between the first and second connection ends 226 and 228, fluidly coupling the connecting portion 220 of the distribution line 214 to the sanitization portion 218 of the distribution line 214. In some instances, the connector 222 may define a channel through which the distribution line 214 passes. In this instance, the distribution line 214 may be a continuous tube that passes through the connector 222, forming a seal therewith, the continuous tube defining each of the hardware portion 216, the sanitization portion 218, and the connecting portion 220.

In some instances, the connecting portion 220 can be configured to couple to a device having one or more internal fluid pathways that is external to the sanitization compartment 202. For example, the connecting portion 220 can include a first section that extends between the hardware portion 216 and the one or more internal fluid pathways of the external device and a second section that extends between the one or more internal fluid pathways of external the device and the sanitization portion 218. In this way, the sanitization device 200 can be utilized to sanitize devices that are too large to be received within the sanitization compartment 202.

The sanitization portion 218 of the distribution line 214 can be configured to fluidly couple to an adaptor 232 (e.g., a mask adaptor) that is disposed within the sanitization compartment 202. The adaptor 232 is configured to distribute ozone gas flowing therethrough along one or more surfaces of a device (or article) to be sanitized 234 (e.g., a mask) disposed within the sanitization compartment 202. In other words, the adaptor 232 can generally be described as being configured to be fluidly coupled to the distribution line 214 such that ozone passes through the adaptor 232 and into the sanitization compartment 202. The adaptor 232 can be configured such that the device 234 physically couples to the adaptor 232 and such that the flow of ozone through the adaptor 232 does not substantially disturb a position of the device 234 relative to the adaptor 232. The adaptor 232 can also have a size and shape that corresponds to that of the device 234 such that the device 234 is consistently positioned within a flow path of the ozone passing through the adaptor 232. For example, when the adaptor 232 is configured to receive a mask, the adaptor 232 may be configured such that, when ozone passes through the adaptor 232, ozone is first incident on a surface of the mask that faces the user when worn.

Figure 3:
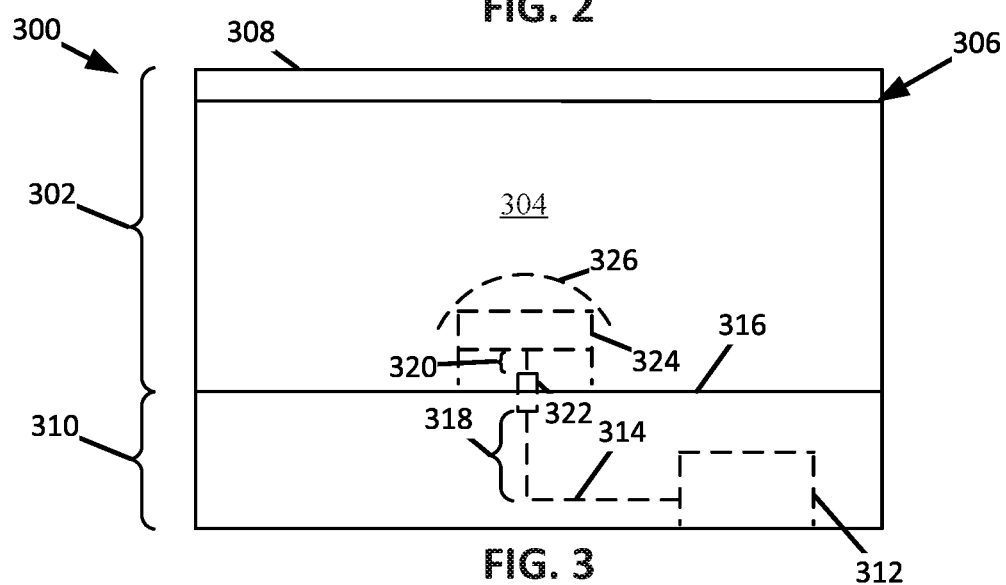
FIG. 3 shows a schematic side view of a sanitization device, which may be another example of the sanitization device of FIG. 1, consistent with embodiments of the present disclosure.

FIG. 3 shows a schematic example of a sanitization device 300, which may be an example of the sanitization device 100 of FIG. 1. As shown, the sanitization device 300 includes a sanitization compartment 302 defining a sanitization cavity 304 having at least one open end 306 and a lid 308 extending over the open end 306 and selectively enclosing the sanitization cavity 304. The sanitization device 300 further includes a hardware compartment 310 for receiving an ozone operating system 312 configured to generate ozone gas to be delivered to the sanitization cavity 304.

As shown, the ozone gas generated by the ozone operating system 312 is delivered to the sanitization compartment 302 through a distribution line 314. The distribution line 314 extends from the ozone operating system 312, within the hardware compartment 310, and directly into the sanitization compartment 302 from the hardware compartment 310. For example, the distribution line 314 can extend directly from the hardware compartment 310 into the sanitization compartment 302 by extending through one or more sidewalls 316 that separate the hardware compartment 310 from the sanitization compartment 302 (e.g., a sidewall defining a base or bottom surface of the sanitization compartment 302). By way of further example, the distribution line 314 may include a hardware portion 318 that extends within the hardware compartment 310 and a sanitization portion 320 that extends within the sanitization compartment 302. A connector 322 may be positioned between the hardware portion 318 and the sanitization portion 320 of the distribution line 314, wherein the connector 322 fluidly couples the hardware portion 318 to the sanitization portion 320. The connector 322 may extend through the one or more sidewalls 316.

The sanitization portion 320 of the distribution line 314 can be configured to fluidly couple to an adaptor 324 (e.g., a mask adaptor). The adaptor 324 is configured to distribute ozone gas flowing therethrough along one or more surfaces of a device (or article) to be sanitized 326 (e.g., a mask) disposed within the sanitization compartment 302. The adaptor 324 can be configured such that the device 326 physically couples to the adaptor 324 and such that the flow of ozone through the adaptor 324 does not substantially disturb a position of the device 326 relative to the adaptor 324. The adaptor 324 can also have a size and shape that corresponds to that of the device 326 such that the device 326 is consistently positioned within a flow path of the ozone passing through the adaptor 324.

In some instances, the sanitization compartment 302 may not include the adaptor 324. In this instance, the device 326 may rest directly on at least one of the one or more sidewalls 316 (e.g., at least one of the one or more sidewalls 316 may define a base or bottom surface of the sanitization compartment 302 and the device 326 may rest directly thereon). Further, in this instance, the distribution line 314 may not include the sanitization portion 320 that extends from the connector 322 and into the sanitization compartment 302. Accordingly, ozone may pass directly from the connector 322 and into the sanitization compartment 302. In this instance, the connector 322 may extend into the sanitization compartment 302 and have an L-shape (e.g., include a 90° bend). The L-shape may encourage the distribution of ozone within the sanitization compartment 302 by encouraging the ozone to be incident on the surfaces defining the sanitization cavity 304.

In some instances, the distribution line 314 may be a continuous tube that extends from the ozone operating system 312 and into the sanitization compartment 302. As such, the sanitization device 300 may not include the connector 322 that extends through the one or more sidewalls 316. Alternatively, the connector 322 may define a channel through which a continuous tube defining the distribution line 314 passes such that a seal is formed therebetween.

Figure 3A:
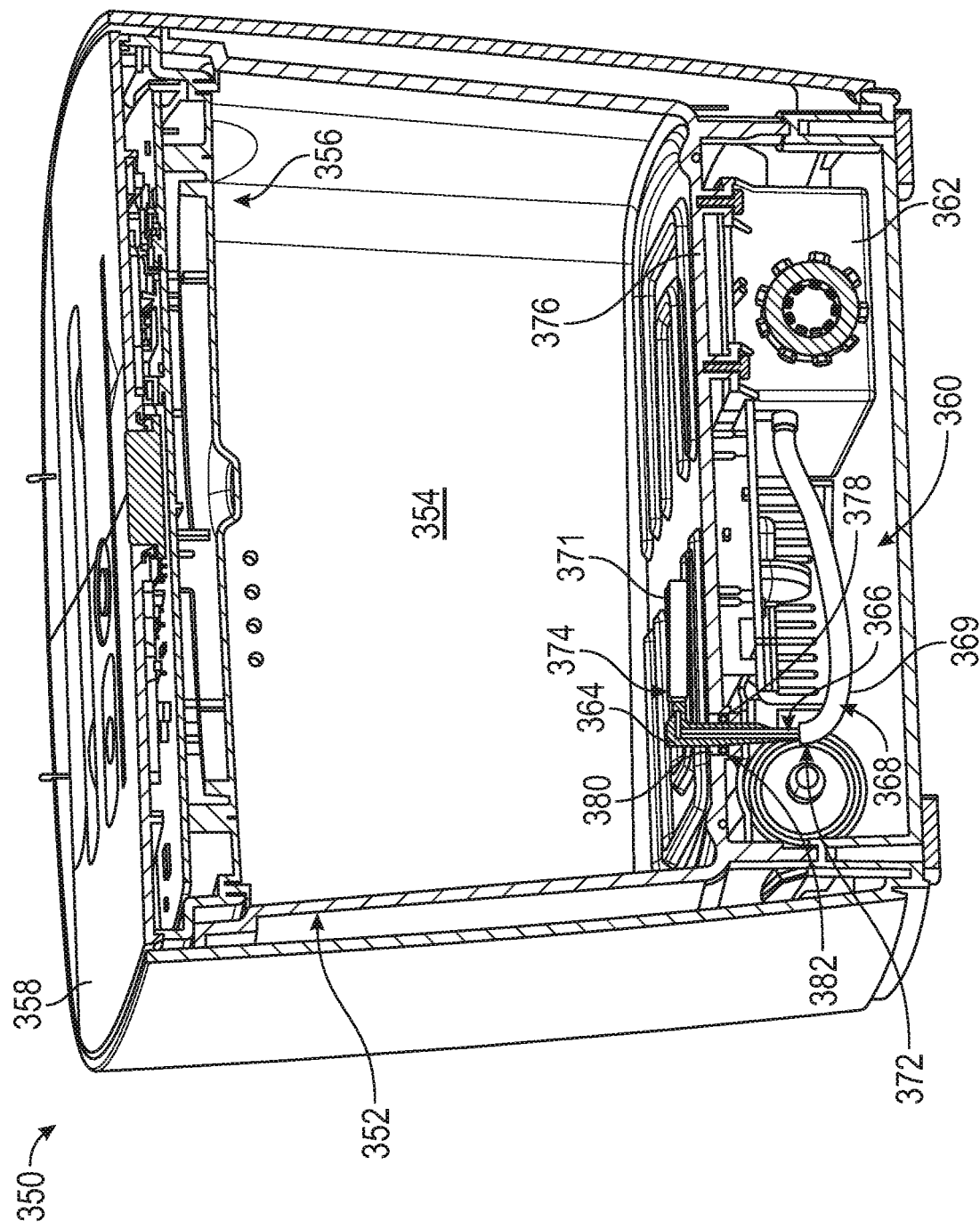
FIG. 3A shows a perspective cross-sectional view of a sanitization device, which may be an example of the sanitization device of FIG. 3, consistent with embodiments of the present disclosure.

FIG. 3A shows a cross-sectional perspective view of a sanitization device 350, which may be an example of the sanitization device 300 of FIG. 3. As shown, the sanitization device 350 includes a sanitization compartment 352 defining a sanitization cavity 354 having at least one open end 356 and a lid 358 extending over the open end 356 and selectively enclosing the sanitization cavity 354. The sanitization device 350 further includes a hardware compartment 360 for receiving an ozone operating system 362 configured to generate ozone gas to be delivered to the sanitization cavity 354.

As shown, a connector 364 extends from the hardware compartment 360 and into the sanitization compartment 352. The connector 364 defines a fluid channel 366 that is configured to fluidly couple the ozone operating system 362 to the sanitization compartment 352 using a distribution line 368. As shown, a first section 369 of the distribution line 368 may extend from the ozone operating system 362 to the connector 364. The first section 369 of the distribution line 368 is configured to couple to the connector 364 at a first end 372 such that ozone passing through the distribution line 368 passes into the fluid channel 366. A second section 371 of the distribution line 368 can couple to the connector 364 at a second end 374 such that ozone flowing through the fluid channel 366 passes into the second section 371 of the distribution line 368. The second section 371 of the distribution line 368 can also be configured to couple to an adaptor (e.g., the adaptor 324 of FIG. 3).

The connector 364 may extend through a sidewall 376 of the sanitization compartment 352, wherein the sidewall 376 extends between the sanitization compartment 352 and the hardware compartment 360. One or more seals 378 may extend around a periphery of the connector 364 and engage with at least a portion of the sidewall 376. For example, the connector 364 may be threadably coupled to the sidewall 376 such that, as the connector 364 is threaded into the sidewall 376, a flange 380 extending from the connector 364 compresses the seal 378 against the sidewall 376. In other words, the seal 378 extends between the flange 380 and the sidewall 376. In this example, the seal 378 may be disposed within a receptacle 382 defined within the sidewall 376. The seal 378 may prevent ozone from entering the hardware compartment 360. As shown, the connector 364 may have an L-shape (e.g., include a 90° bend), wherein the first and second ends 372 and 374 may include a barbed region for engaging an inner surface of the first and second sections of the distribution line 368.

In some instances, the distribution line 368 may be a continuous tube that extends from the ozone operating system 362 and into the sanitization compartment 352. As such, the sanitization device 350 may not include the connector 364 that extends through the sidewall 376. Alternatively, the connector 364 may define a channel through which a continuous tube defining the distribution line 368 passes such that a seal is formed therebetween.

Figure 4:
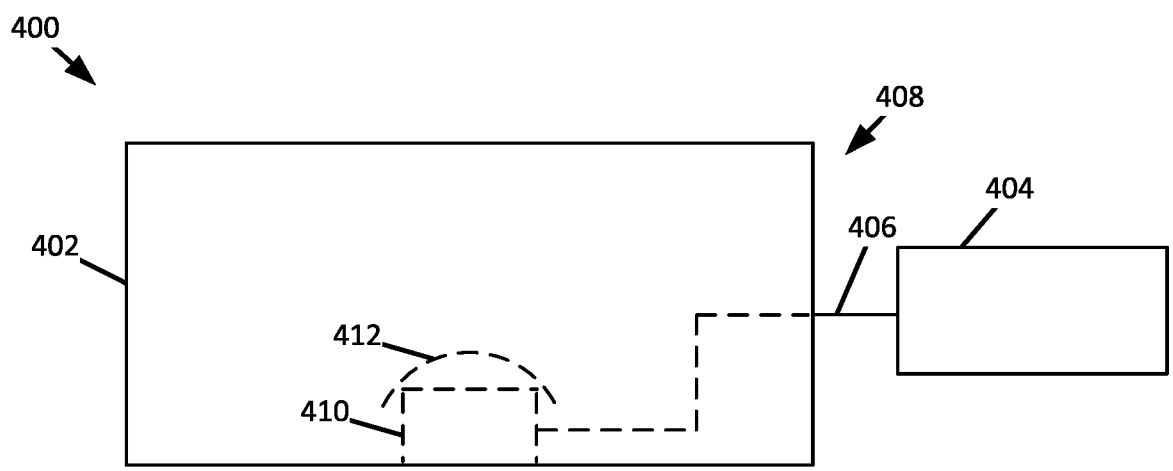
FIG. 4 shows a schematic side view of a sanitization device, which may be another example of the sanitization device of FIG. 1, consistent with embodiments of the present disclosure.

FIG. 4 shows a schematic example of a sanitization device 400, which may be an example of the sanitization device 100 of FIG. 1. As shown, the sanitization device 400 includes a sanitization compartment 402 and an ozone operating system 404 that is separate from the sanitization compartment 402. A distribution line 406 fluidly couples the ozone operating system 404 to the sanitization compartment 402.

In some instances, the sanitization compartment 402 is a flexible bag having at least one selectively sealable open end 408. For example, the sanitization compartment 402 may be a flexible bag having a zip-type connector at the open end 408, wherein the zip-type connector selectively seals the flexible bag at the open end 408.

The distribution line 406 can be configured to be fluidly coupled to an adaptor 410 (e.g., a mask adaptor). The adaptor 410 is configured to distribute ozone gas flowing therethrough along one or more surfaces of a device (or article) to be sanitized 412 (e.g., a mask) disposed within the sanitization compartment 402. The adaptor 410 can be configured such that the device 412 physically couples to the adaptor 410 and such that the flow of ozone through the adaptor 410 does not substantially disturb a position of the device 412 relative to the adaptor 410. The adaptor 410 can also have a size and shape that corresponds to that of the device 412 such that the device 412 is consistently positioned within a flow path of the ozone passing through the adaptor 410.

Figure 5:
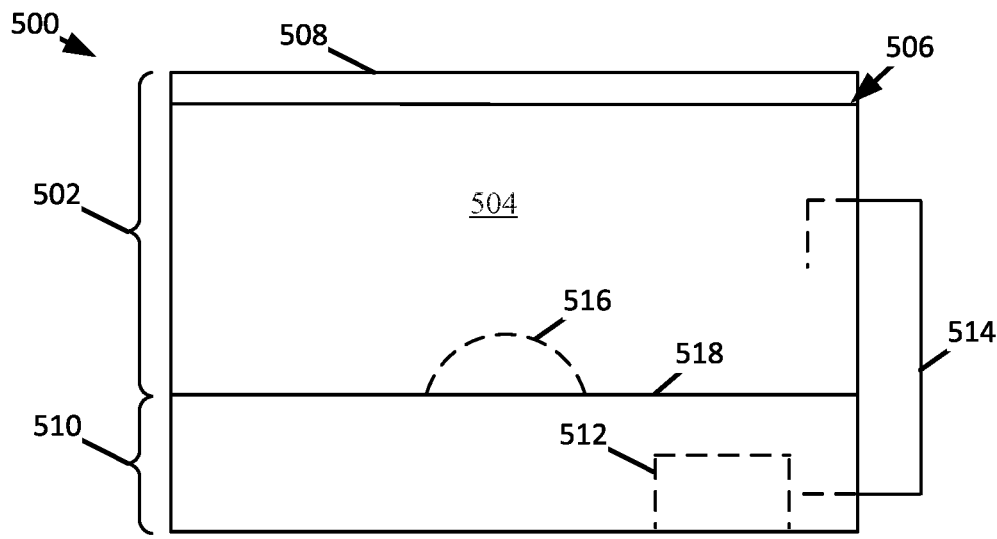
FIG. 5 shows a schematic side view of a sanitization device, which may be another example of the sanitization device of FIG. 1, consistent with embodiments of the present disclosure.

FIG. 5 shows a schematic example of a sanitization device 500, which may be an example of the sanitization device 100 of FIG. 1. As shown, the sanitization device 500 includes a sanitization compartment 502 defining a sanitization cavity 504 having at least one open end 506, and a lid 508 extending over the open end 506 and selectively enclosing the sanitization cavity 504. The sanitization device 500 further includes a hardware compartment 510 for receiving an ozone operating system 512 configured to generate ozone gas to be delivered to the sanitization cavity 504.

As shown, a distribution line 514 fluidly couples the ozone operating system 512 to the sanitization compartment 502 such that ozone flows into the sanitization compartment 502. The distribution line 514 can be configured to disperse ozone directly into the sanitization compartment 502. In this instance, ozone saturates the sanitization compartment 502 such that one or more objects 516 (e.g., one or more masks) positioned therein are exposed to the ozone. For example, the one or more objects 516 may rest directly on a sidewall 518 (e.g., a bottom sidewall) of the sanitization compartment 502.

Figure 6:
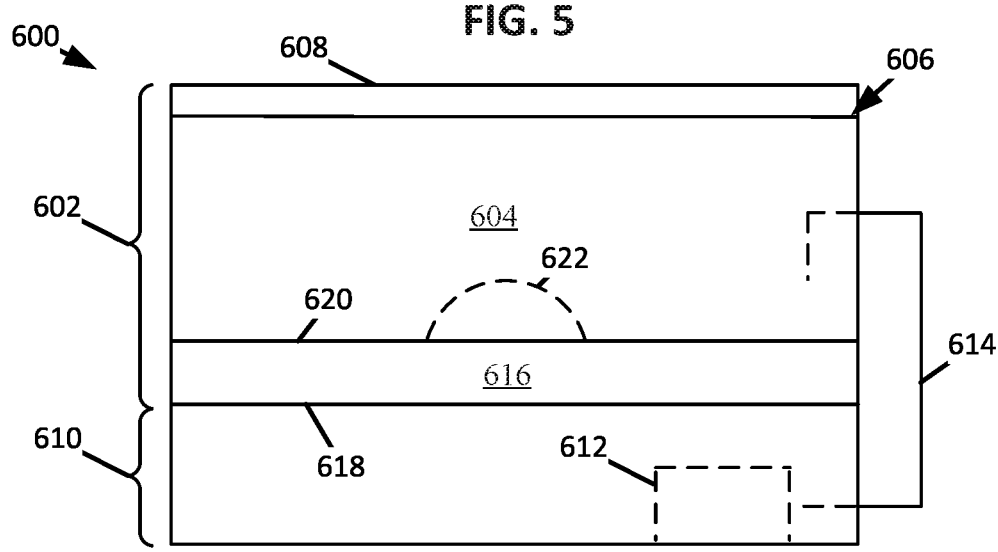
FIG. 6 shows a schematic side view of a sanitization device, which may be another example of the sanitization device of FIG. 1, consistent with embodiments of the present disclosure.

FIG. 6 shows a schematic example of a sanitization device 600, which may be an example of the sanitization device 100 of FIG. 1. As shown, the sanitization device 600 includes a sanitization compartment 602 defining a sanitization cavity 604 having at least one open end 606, and a lid 608 extending over the open end 606 and selectively enclosing the sanitization cavity 604. The sanitization device 600 further includes a hardware compartment 610 for receiving an ozone operating system 612 configured to generate ozone gas to be delivered to the sanitization cavity 604.

As shown, a distribution line 614 fluidly couples the ozone operating system 612 to the sanitization compartment 602 such that ozone flows into the sanitization compartment 602. The distribution line 614 can be configured to disperse ozone directly into the sanitization compartment 602. As shown, the sanitization compartment 602 can include a plenum 616 that is defined between a sidewall 618 (e.g., a bottom sidewall) of the sanitization compartment 602 and a support surface 620 of the sanitization compartment 602. The support surface 620 can include a plurality of apertures (e.g., such that the supporting surface 620 can generally be described as including a grate) through which ozone can pass. As such, when one or more objects 622 are disposed on (e.g., directly on) the support surface 620, ozone gas can flow through the plurality of apertures and into contact with the one or more objects 622. As such, ozone gas can come into contact with opposing sides of the one or more objects 622. In some instances, the support surface 620 may be made of an ozone permeable material.

Figure 7:
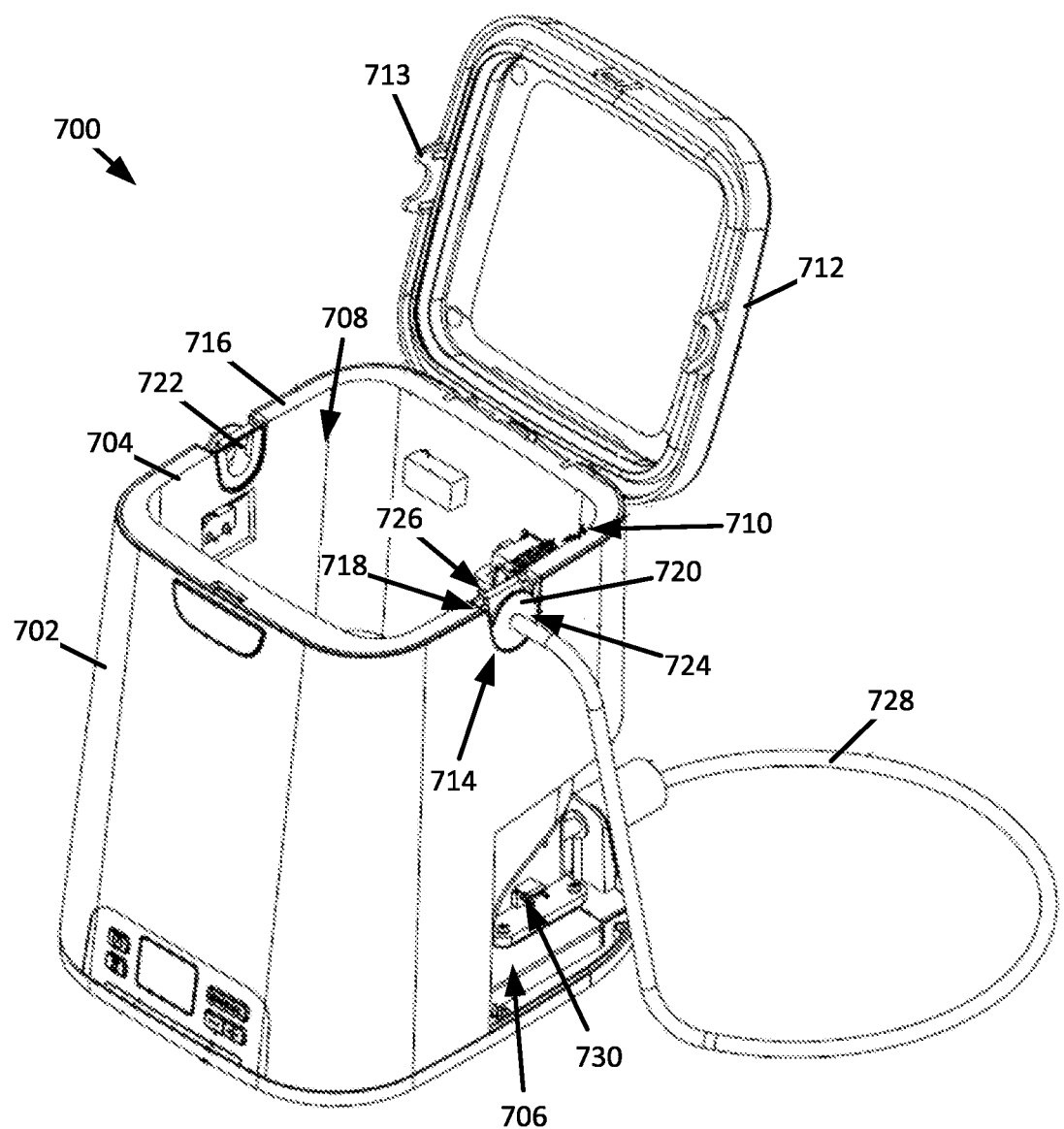
FIG. 7 shows a perspective view of a sanitization device, which may be another example of the sanitization device of FIG. 1, consistent with embodiments of the present disclosure.

FIG. 7 shows a perspective view of a sanitization device 700, which may be an example of the sanitization device 100 of FIG. 1. As shown, the sanitization device 700 includes a device body 702 defining a sanitization compartment 704 and a hardware compartment 706. The sanitization compartment 704 defines a sanitization cavity 708 having at least one cavity open end 710. The sanitization compartment 704 is configured to receive one or more devices (e.g., one or more masks) through the cavity open end 710. A lid 712 is configured to transition between an open position in which the cavity open end 710 is exposed to the environment and a closed position in which the lid 712 extends over the cavity open end 710. As such, the lid 712 can generally be described as selectively enclosing the sanitization compartment 704.

One or more passageways 714 can extend through a corresponding one or more sidewalls 716 of the device body 702. The one or more passageways 714 may include a passageway open end 718 that opens in a direction of the lid 712 when the lid 712 is in the closed position. The one or more passageways 714 can be configured to receive a connector 720 or a plug 722 when the lid 712 is in the open position. For example, and as shown, when the one or more sidewalls 716 include a plurality of passageways 714, the connector 720 can be received within a first passageway 714 and the plug 722 can be configured to be received within a second passageway 714. When in the closed position, the lid 712 sealingly engages with a portion of the connector 720 and/or plug 722 such that ozone gas is substantially prevented from escaping from the one or more passageways 714. For example, and as shown, the lid 712 may include engaging features 713 that have a shape that generally corresponds to the shape of the connector 720 and plug 722.

The connector 720 can define a fluid channel that extends from a first end 724 to a second end 726 of the connector 720, wherein the fluid channel is configured to fluidly couple to a distribution line 728. In other words, the connector 720 can generally be described as being fluidly coupled to the distribution line 728. The distribution line 728 includes a first section that is external to the sanitization compartment 704 and that is fluidly coupled to an ozone operating system 730 disposed within the hardware compartment 706. The first section of the distribution line 728 extends between the first end 724 of the connector 720 and the ozone operating system 730. The distribution line 728 may also include a second section that extends from the second end 726 of the connector 720 and into the sanitization compartment 704. In operation, the ozone operating system 730 generates ozone gas and urges the ozone gas along the distribution line 728 and into the sanitization compartment 704.

The plug 722 may include a body (e.g., a solid body) through which ozone is substantially prevented from passing through. In some instances, the plug 722 may be configured to provide an electrical coupling to one or more devices (e.g., one or more fans) disposed within the sanitization compartment 704. For example, the plug 722 may be configured to have one or more wires pass therethrough, wherein the plug sealingly engages with the one or more wires such that ozone is substantially prevented from flowing through the plug 722 at a location adjacent the one or more wires. The plug 722 and the connector 720 are interchangeable. As such, and as shown, when there are a plurality of passageways 714, the location of the connector 720 may be adjusted such that a position of the distribution line 728 may be adjusted.

Figure 9:
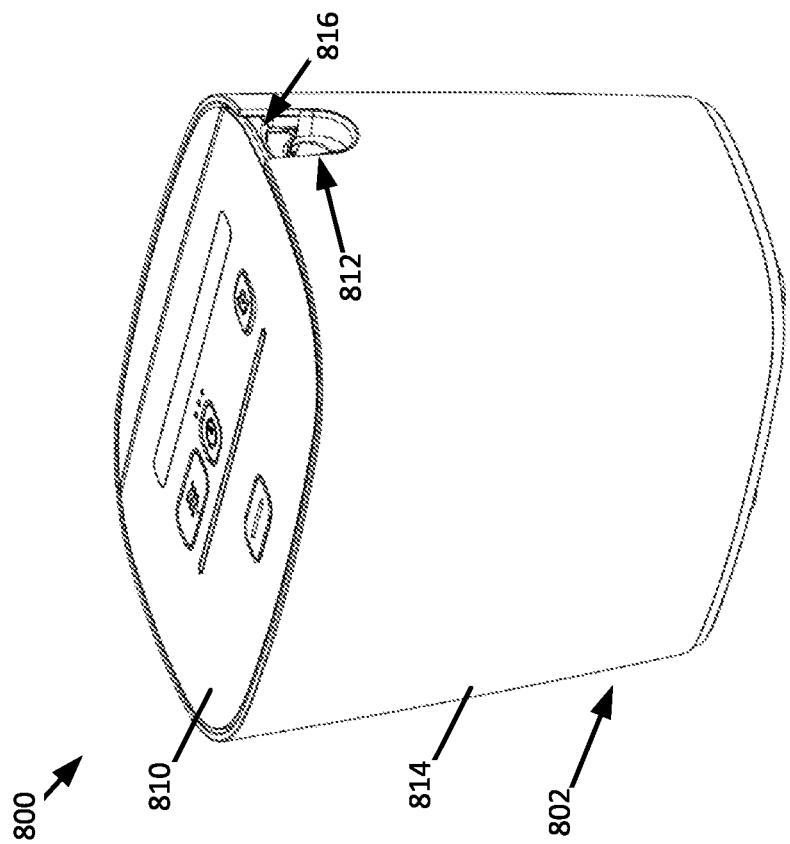
FIG. 9 shows a perspective view of the sanitization device of FIG. 8 having the lid in the closed position, consistent with embodiments of the present disclosure.
Figure 8:
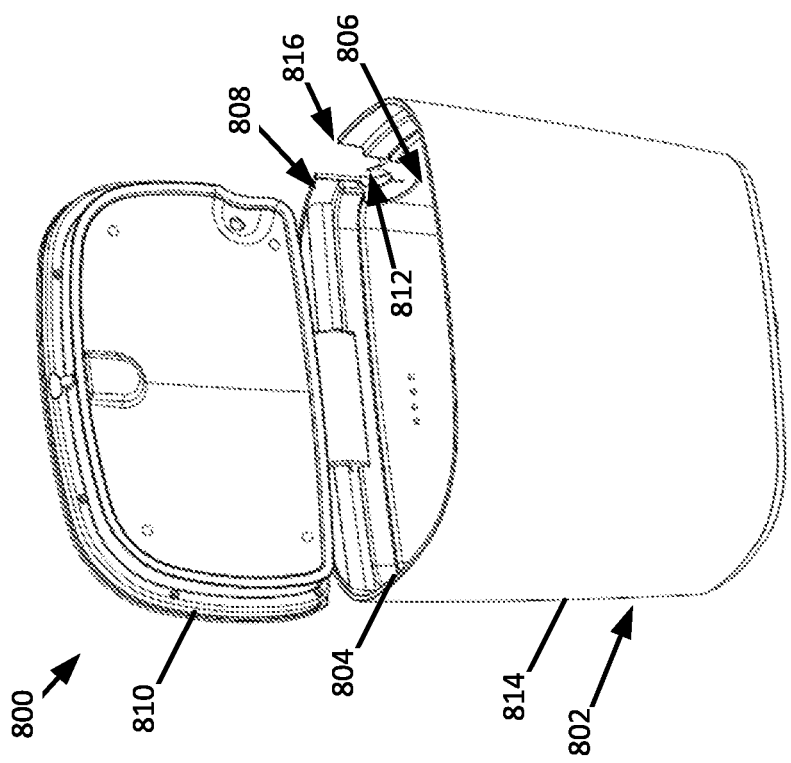
FIG. 8 shows a perspective view of a sanitization device having a lid in an open position, the sanitization device may be another example of the sanitization device of FIG. 1, consistent with embodiments of the present disclosure.

FIG. 8 shows a perspective view of a sanitization device 800, which may be an example of the sanitization device 100 of FIG. 1. As shown, the sanitization device 800 includes a device body 802 defining a sanitization compartment 804. The sanitization compartment 804 defines a sanitization cavity 806 having at least one cavity open end 808. The sanitization compartment 804 is configured to receive one or more devices (e.g., one or more masks) through the cavity open end 808. A lid 810 is configured to transition between an open position (e.g., as shown in FIG. 8) in which the cavity open end 808 is exposed to the environment and a closed position (e.g., as shown in FIG. 9) in which the lid 810 extends over the cavity open end 808. As such, the lid 810 can generally be described as selectively enclosing the sanitization compartment 804.

One or more passageways 812 can extend through a corresponding one or more sidewalls 814 of the device body 802. The one or more passageways 812 may include a passageway open end 816 that opens in a direction of the lid 810 when the lid 810 is in the closed position. The one or more passageways 812 can be configured to receive a connector or a plug when the lid 810 is in the open position. When the lid 810 is in the closed position, the lid 810 engages the connector or plug such that a seal is formed therebetween.

Figure 10:
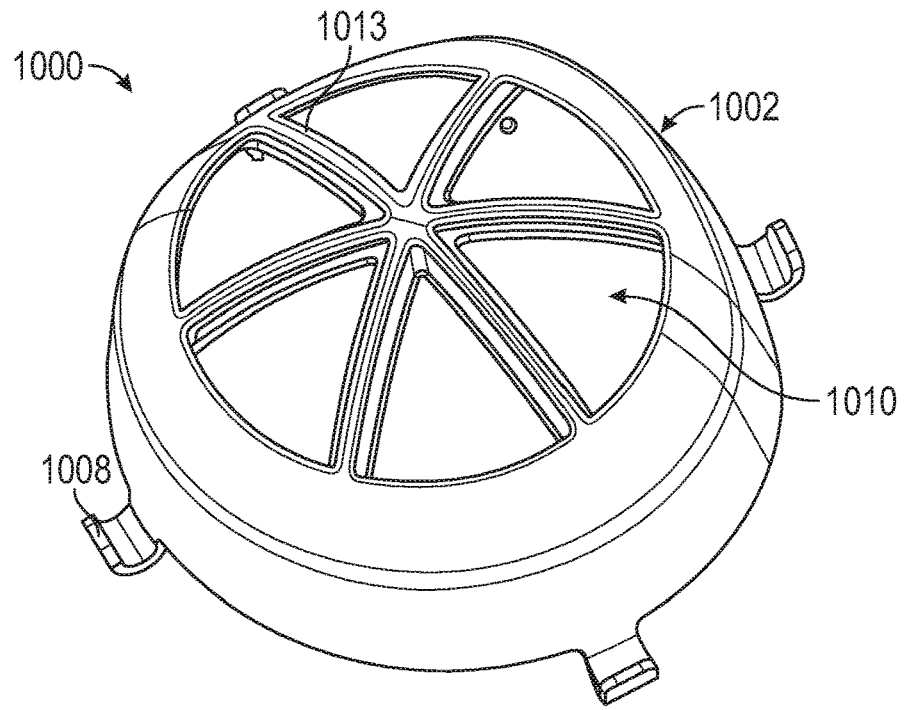
FIG. 10 shows a perspective top view of an adaptor configured to hold a mask, consistent with embodiments of the present disclosure.
Figure 11:
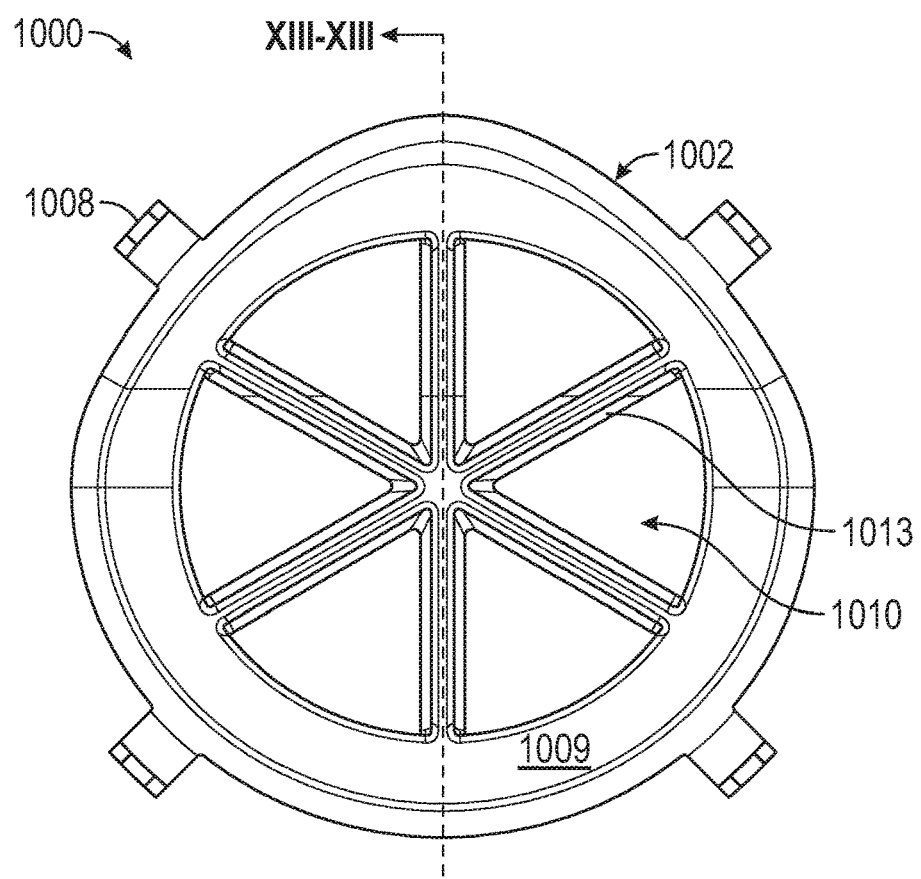
FIG. 11 shows a top view of the adaptor of FIG. 10, consistent with embodiments of the present disclosure.
Figure 12:
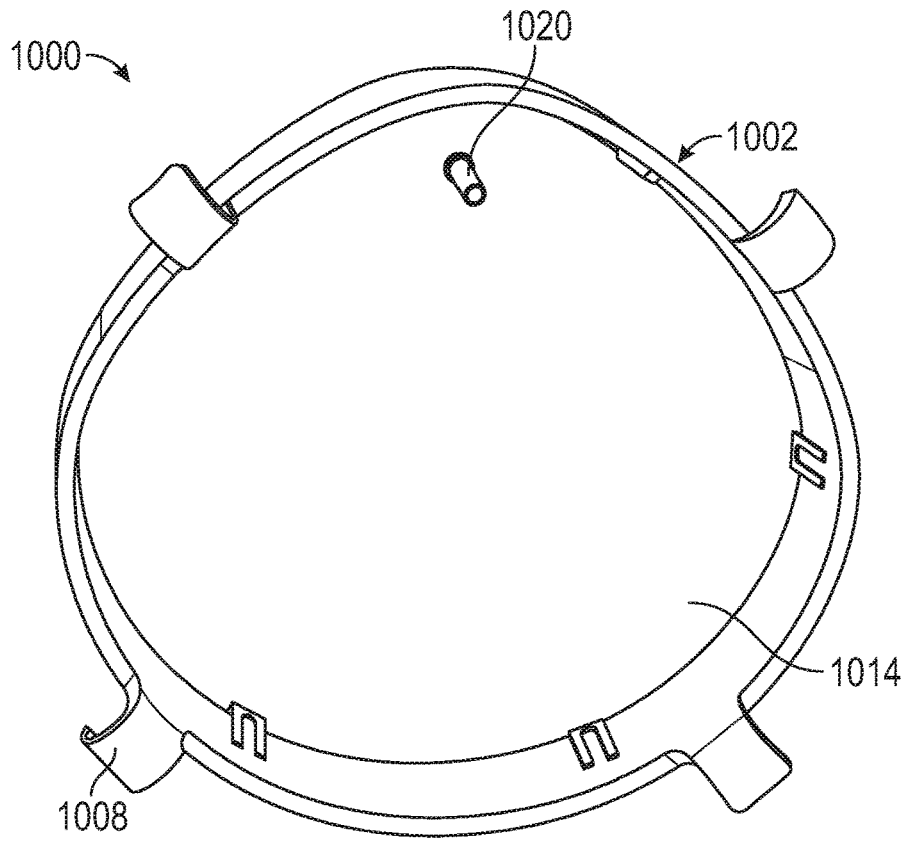
FIG. 12 shows a perspective bottom view of the adaptor of FIG. 10, consistent with embodiments of the present disclosure.
Figure 13:
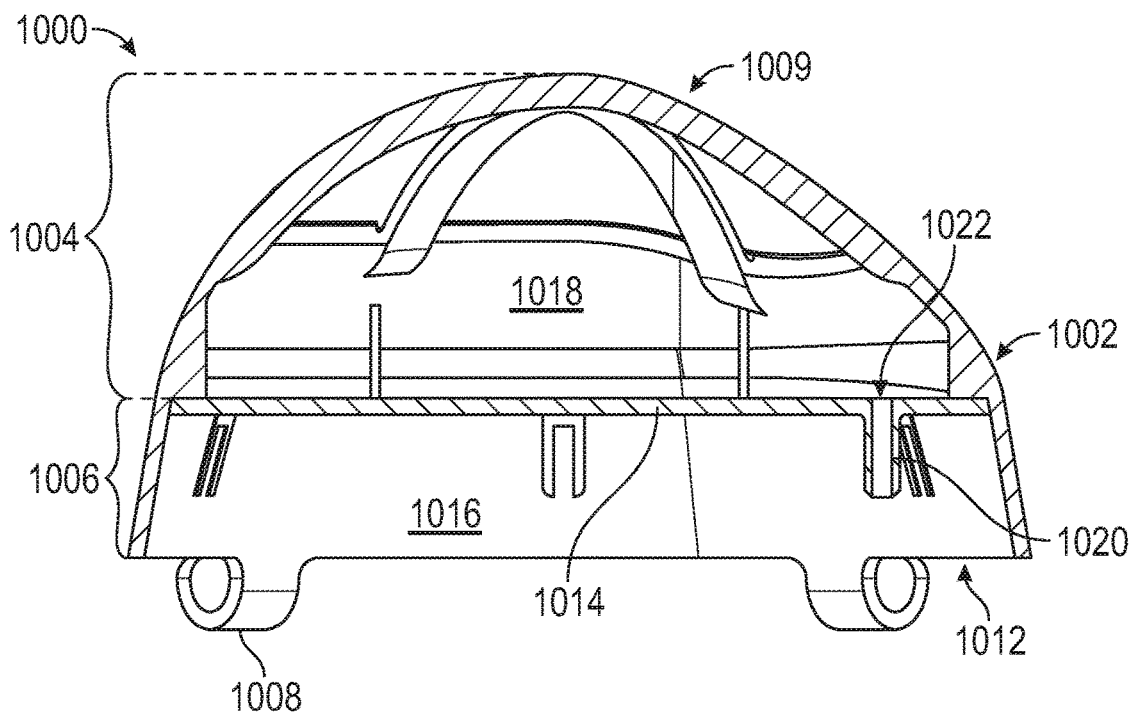
FIG. 13 shows a cross-sectional view of the adaptor of FIG. 10 taken along the line XIII-XIII of FIG. 11, consistent with embodiments of the present disclosure.

FIG. 10 shows a perspective top view of an adaptor 1000 configured to hold a mask (which may generally be referred to as a mask adaptor), FIG. 11 shows a top view of the adaptor 1000, FIG. 12 shows a bottom perspective view of the adaptor 1000, and FIG. 13 shows a cross-sectional view of the adaptor 1000 taken along the line XIII-XIII of FIG. 11. The adaptor 1000 may be an example of any one or more of the adaptors 232, 324, and/or 410 of FIGS. 2-4.

As shown, the adaptor 1000 includes an adaptor body 1002 that includes a mask supporting region 1004 and a base region 1006. A plurality of supports 1008 extend from the base region 1006 and are configured to support the adaptor body 1002. For example, the supports 1008 can support the adaptor body 1002 such that the base region 1006 is spaced apart from a supporting surface within a sanitization device (e.g., the sanitization device 100 of FIG. 1). The supports 1008 can have an arcuate shape. An arcuate shaped support 1008 may have a first portion that curves away from the adaptor body 1002 and a second portion that curves towards the adaptor body 1002. In other words, arcuate shaped supports 1008 can generally be described as having a hook-shape.

The mask supporting region 1004 may have a shape that generally corresponds to a shape of a mask supported thereby. For example, at least a substantial portion (e.g., at least 75%, at least 80%, at least 85%, at least 90%, at least 95%, at least 99%, or 100%) of a mask facing surface 1009 of the mask supporting region 1004 may be in direct contact with the mask supported thereby.

The mask supporting region 1004 has one or more apertures 1010 that extend through the adaptor body 1002 and into an adaptor cavity 1012 defined within the adaptor body 1002. The one or more apertures 1010 are configured such that ozone can flow from the adaptor cavity 1012 through the one or more apertures 1010 and into engagement with a mask disposed on the mask supporting region 1004. For example, when an air-permeable mask (e.g., a medical N95 compliant mask), is disposed on the mask supporting region 1004, ozone is caused to flow from the adaptor cavity 1012, through both the one or more apertures 1010 and the air-permeable mask, and into, for example, a sanitization compartment (e.g., the sanitization compartment 104). In some instances, the adaptor 1000 may include a fan configured to urge ozone through the one or more apertures 1010. Such a configuration may encourage more rapid migration of ozone through a mask supported by the mask supporting region 1004. Additionally, or alternatively, after completion of sanitization (i.e., ozone is no being generated by the ozone operating system) the fan may be used to urge ozone and/or any outgasses from the materials forming the mask from the material of the mask.

In some instances, the mask supporting region 1004 can include a plurality apertures 1010 (e.g., triangular shaped apertures), wherein a support rib 1013 extends between immediately adjacent apertures 1010. The support rib 1013 may have a shape that generally corresponds to a shape of a mask to be supported thereby (e.g., a generally arcuate shape). The apertures 1010 and support rib(s) 1013 can be sized such that ozone can freely flow through the apertures and through a mask supported by the support rib(s) 1013 and such that the supported mask can be adequately sanitized by the flow of ozone gas.

An ozone distribution plate 1014 can extend within the adaptor cavity 1012, separating the adaptor cavity 1012 into a first cavity region 1016 and a second cavity region 1018. As shown, the ozone distribution plate 1014 can be coupled to the adaptor body 1002 using a snap-fit connection. Additionally, or alternatively, the ozone distribution plate 1014 can be coupled to the adaptor body 1002 using, for example, any one or more of adhesives, threaded connections, and/or any other type of coupling.

The ozone distribution plate 1014 can include an ozone port 1020 configured to facilitate a flow of ozone into the second cavity region 1018 through an ozone channel 1022 defined in the ozone port 1020. For example, the ozone port 1020 can be configured to couple to a distribution line (e.g., the distribution line 214, 314, 406, and/or 728) that is fluidly coupled to an ozone operating system (e.g., the ozone operating system 102). In this example, ozone first flows into the second cavity region 1018 and then passes through the one or more apertures 1010 and into a mask disposed on the mask supporting region 1004 of the adaptor 1000. Once the ozone passes through the mask, the ozone may diffuse throughout the sanitization compartment and into the first cavity region 1016. Accordingly, the ozone distribution plate 1014 may generally be described as being configured to cause ozone gas to flow into the second cavity region 1018 before flowing through the one or more apertures 1010. In some instances, the ozone port 1020 directly fluidly couples the distribution line to the second cavity region 1018.

Figure 14:
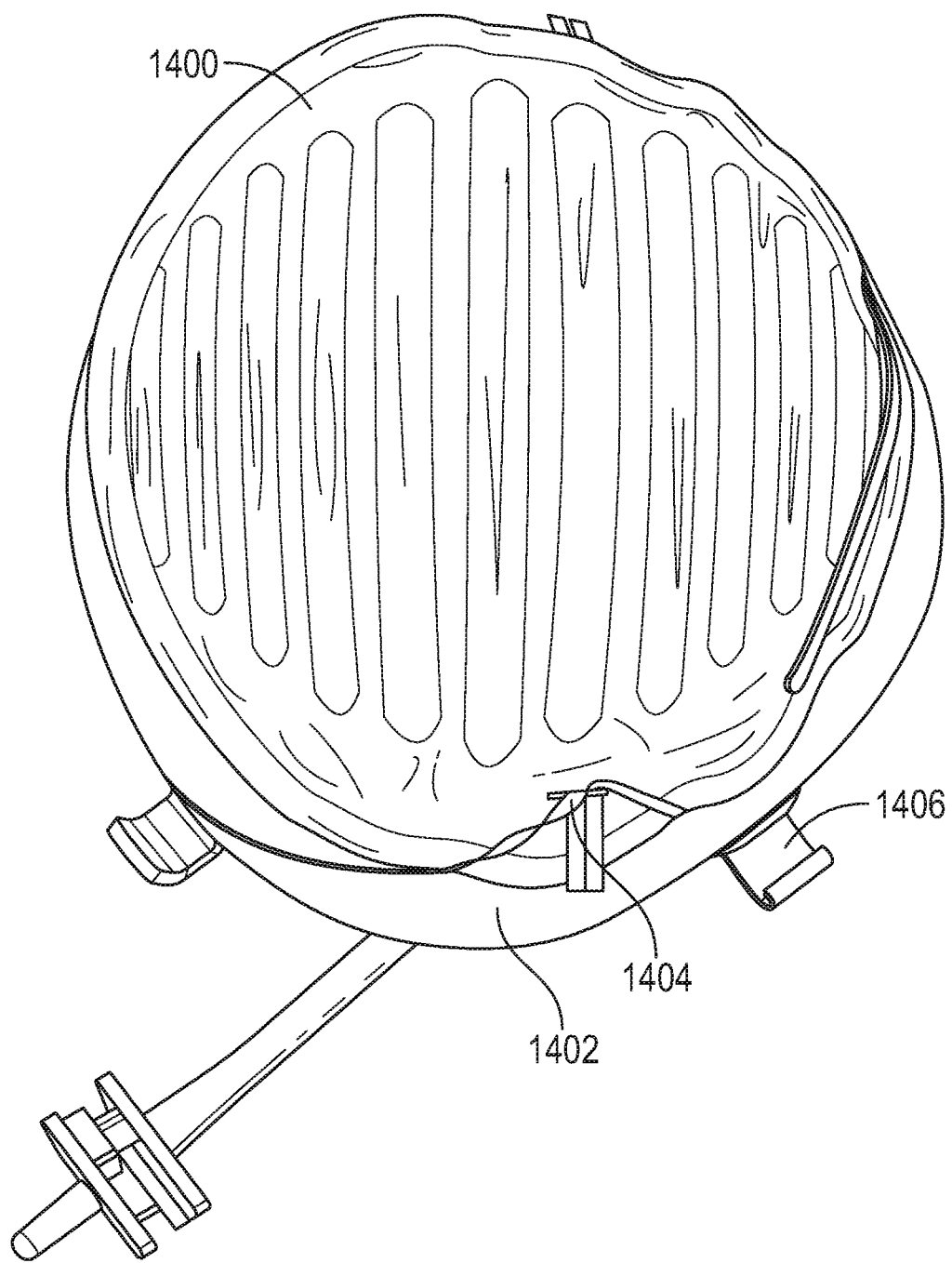
FIG. 14 shows a perspective view of a mask coupled to an adaptor configured to hold a mask, consistent with embodiments of the present disclosure.

FIG. 14 shows a perspective view of an air-permeable mask 1400 disposed on a mask adaptor 1402, which may be an example of the adaptor 1000 of FIG. 10. As shown, the adaptor 1402 has a shape that generally corresponds to that of the mask 1400. The mask 1400 includes one or more elastic bands 1404 configured to expand around a user's head and hold the mask 1400 against a user's face with sufficient force to retain the mask 1400 in place. When the mask 1400 is disposed on the mask adaptor 1402, the one or more elastic bands 1404 can be used to couple the mask 1400 to the mask adaptor 1402. As such, when ozone passes through the mask adaptor 1402, the mask 1400 is held in place such that a flow of ozone does not significantly disturb a position of the mask 1400 relative to the mask adaptor 1402.

For example, the mask 1400 can be coupled to the mask adaptor 1402 by wrapping one or more of the one or more elastic bands 1404 around one or more supports 1406 of the mask adaptor 1402. In other words, when one or more of the one or more elastic bands 1404 extend around one or more of the supports 1406, the mask 1400 can generally be described as being coupled to the mask adaptor 1402. As such, the supports 1406 can generally be described as being configured to support the mask adaptor 1402 and to couple the mask 1400 to the mask adaptor 1402. By way of further example, the mask 1400 can be coupled to the mask adaptor 1402 by wrapping one or more of the one or more elastic bands 1404 around one or more coupling protrusions extending from the mask adaptor 1402. By way of still further example, the mask 1400 can be coupled to the mask adaptor 1402 using one or more clamping mechanisms.

Use of the one or more elastic bands 1404 to couple the mask 1400 to the mask adaptor 1402 may maximize the surface area of the mask 1400 exposed to ozone gas during the sanitization process. By way of comparison, when a clamping mechanism is used, the clamping mechanism engages a portion of the mask which may reduce the sanitization efficiency at the clamping locations along the mask 1400 (e.g., longer exposure to ozone gas may be required to obtain adequate sanitization as a result of use of a clamping mechanism).

Figure 15:
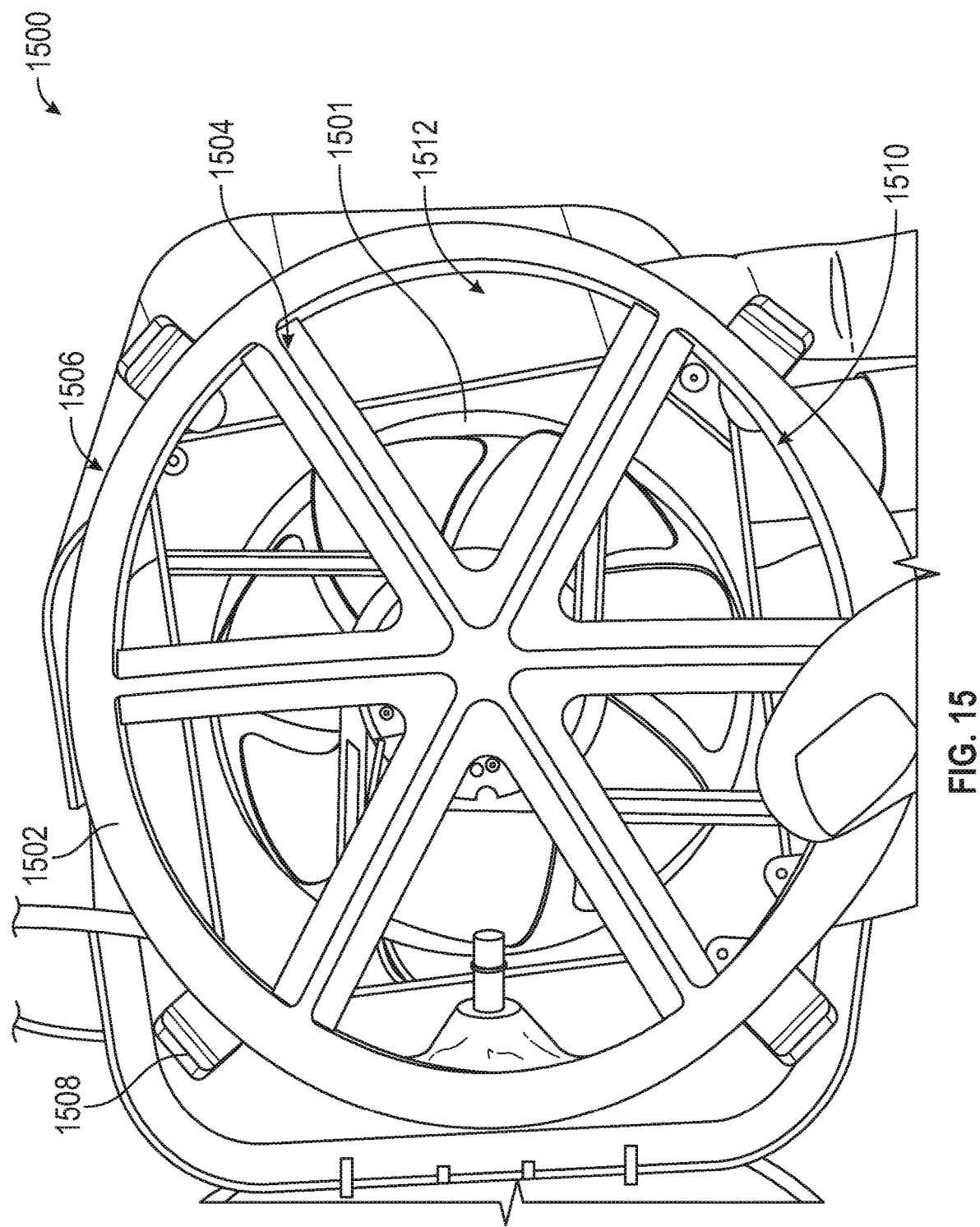
FIG. 15 shows a top view of an example of an adaptor, consistent with embodiments of the present disclosure.

FIG. 15 shows a top view of a mask adaptor 1500, which may be an example of the adaptor 1000 of FIG. 10, wherein the ozone distribution plate 1014 includes or is replaced by a fan 1501. As shown, the adaptor 1500 includes an adaptor body 1502 that includes a mask supporting region 1504 and a base region 1506. A plurality of supports 1508 extend from the base region 1506 and are configured to support the adaptor body 1502. The mask supporting region 1504 may have a shape that generally corresponds to a shape of a mask supported thereby. The mask supporting region 1504 has one or more apertures 1510 that extend through the adaptor body 1502 and into an adaptor cavity 1512 defined within the adaptor body 1502. The one or more apertures 1510 are configured such that ozone can flow from the adaptor cavity 1512 through the one or more apertures 1510 and into engagement with a mask disposed on the mask supporting region 1504.

As shown, the fan 1501 is disposed within the adaptor cavity 1512. The fan 1501 is configured to encourage air and/or ozone to flow through the one or more apertures 1510. During the sanitization process, the fan 1501 may encourage ozone to flow through a mask supported by the mask supporting region 1504. Additionally, or alternatively, after the sanitization process (i.e., after ozone generation has ceased) the fan 1501 may encourage air to flow through a mask supported by the mask supporting region 1504. As such, any residual ozone trapped within the materials of the mask may be urged from the mask. Further, in some instances, when ozone passes through the materials of the mask, the ozone may react with the materials resulting in the generation of additional gasses (some of which may have an unpleasant odor). In this instance, when the fan 1501 encourages air to flow through the mask, these additional gasses may be urged from the materials of the mask.

Figure 16:
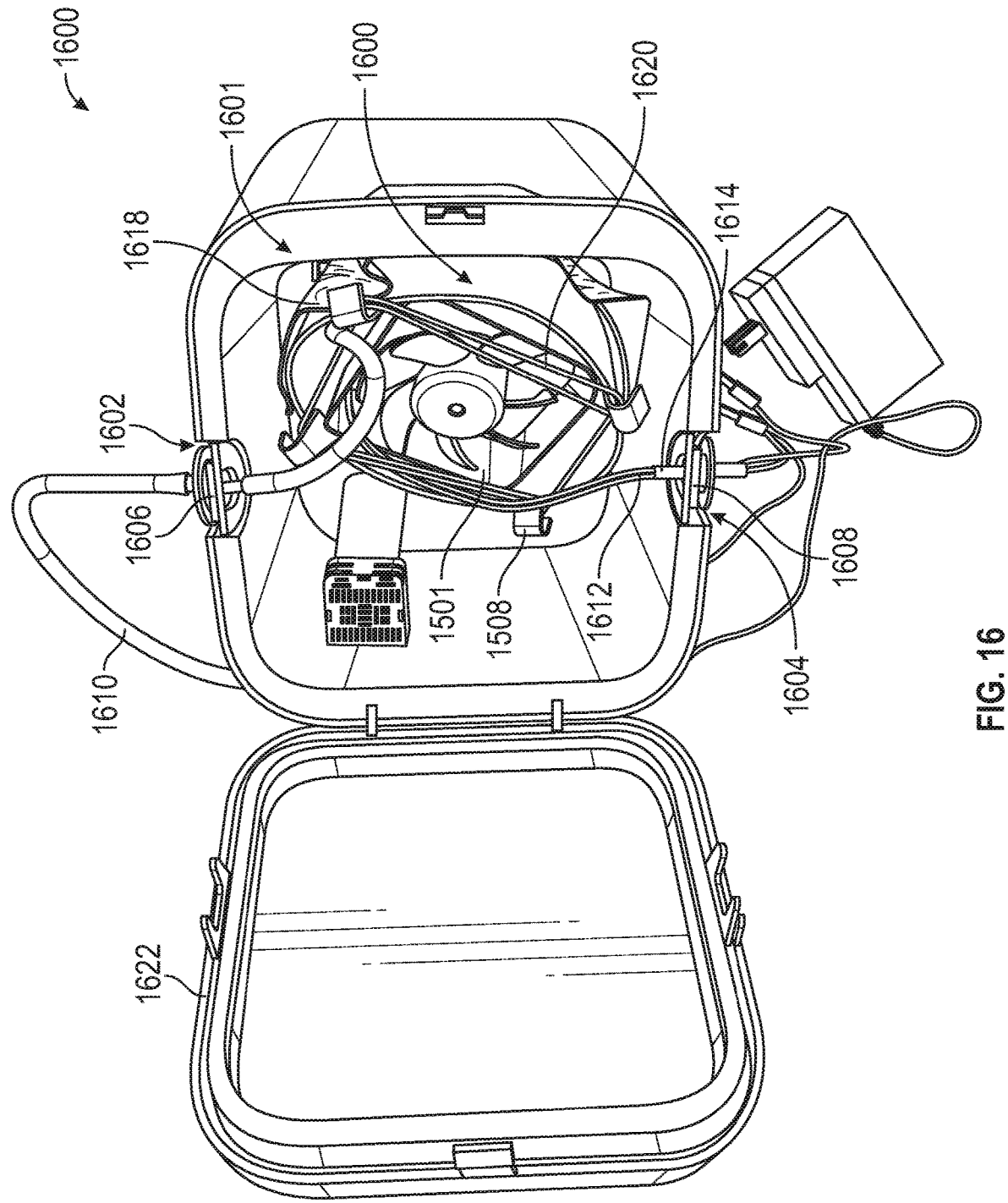
FIG. 16 shows a perspective view of the adaptor of FIG. 15 in a sanitization device, consistent with embodiments of the present disclosure.

FIG. 16 shows a perspective view of the adaptor 1500 disposed within a sanitization compartment 1601 of a sanitization device 1600, which may be an example of the sanitization device 700 of FIG. 7. The sanitization device 1600 includes a first passageway 1602 and a second passageway 1604. As shown, the first passageway 1602 is configured to receive a connector 1606 and the second passageway 1604 is configured to receive a plug 1608. The connector 1606 defines a fluid channel for fluidly coupling a first portion of a distribution line 1610 to a second portion of the distribution line 1610. As shown, the distribution line 1610 couples to the adaptor 1500 at a location proximate to the fan 1501 such that ozone exiting the distribution line 1610 can be carried within a flow path generated by the fan 1501.

The plug 1608 includes one or more wires 1612 extending therethrough, the one or more wires 1612 being configured to electrically couple to the fan 1501. The plug 1608 is configured to sealingly engage with the one or more wires 1612 such that ozone is substantially prevented from passing through the plug 1608 at a location adjacent the one or more wires 1612. For example, the plug 1608 may include a plurality of wire guides 1614, wherein each wire guide 1614 extends from an opposing side of the plug 1608. The wire guides 1614 are configured such that the one or more wires 1612 can extend therethrough. In some instances, the wire guides 1614 can comprise a material that contracts when exposed to heat such that, when the one or more wires 1612 are received within and extend through the wire guides 1614, the wire guides 1614 can be exposed to a heat source causing the wire guides 1614 to contract about the one or more wires 1612, forming a seal therebetween. Additionally, or alternatively, a sealant (e.g., an adhesive) may be applied to the distal end of one or more of the wire guides 1614 such that a seal can be formed between the one or more wires and a corresponding distal end of the wire guides 1614. In some instances, the fan 1501 may be powered through an electrical coupling defined within the sanitization compartment 1601 of the sanitization device 1600 instead of from wires passing through the plug 1608.

As shown, a mask 1618 is coupled to the adaptor 1500. The mask 1618 can be coupled to the adaptor 1500 by wrapping one or more elastic bands 1620 of the mask 1618 around one or more of the supports 1508.

In some instances, the fan 1501 may include and/or be coupled to one or more fan safety devices. For example, a plate or grate may extend over at least a portion of one or more blades of the fan 1501. By way of further example, the fan 1501 can be configured to be turned off when a lid 1622 of the sanitization device 1600 is in an open position. As such, a risk of the fan 1501 harming a user may be reduced when using one or more fan safety devices. In some instances, the adaptor 1500 may include one or more orienting features configured to orient the adaptor 1500 within the sanitization device 1600. The orienting features may allow ozone to more readily flow through the adaptor 1500 and the mask 1618.

Figure 17:
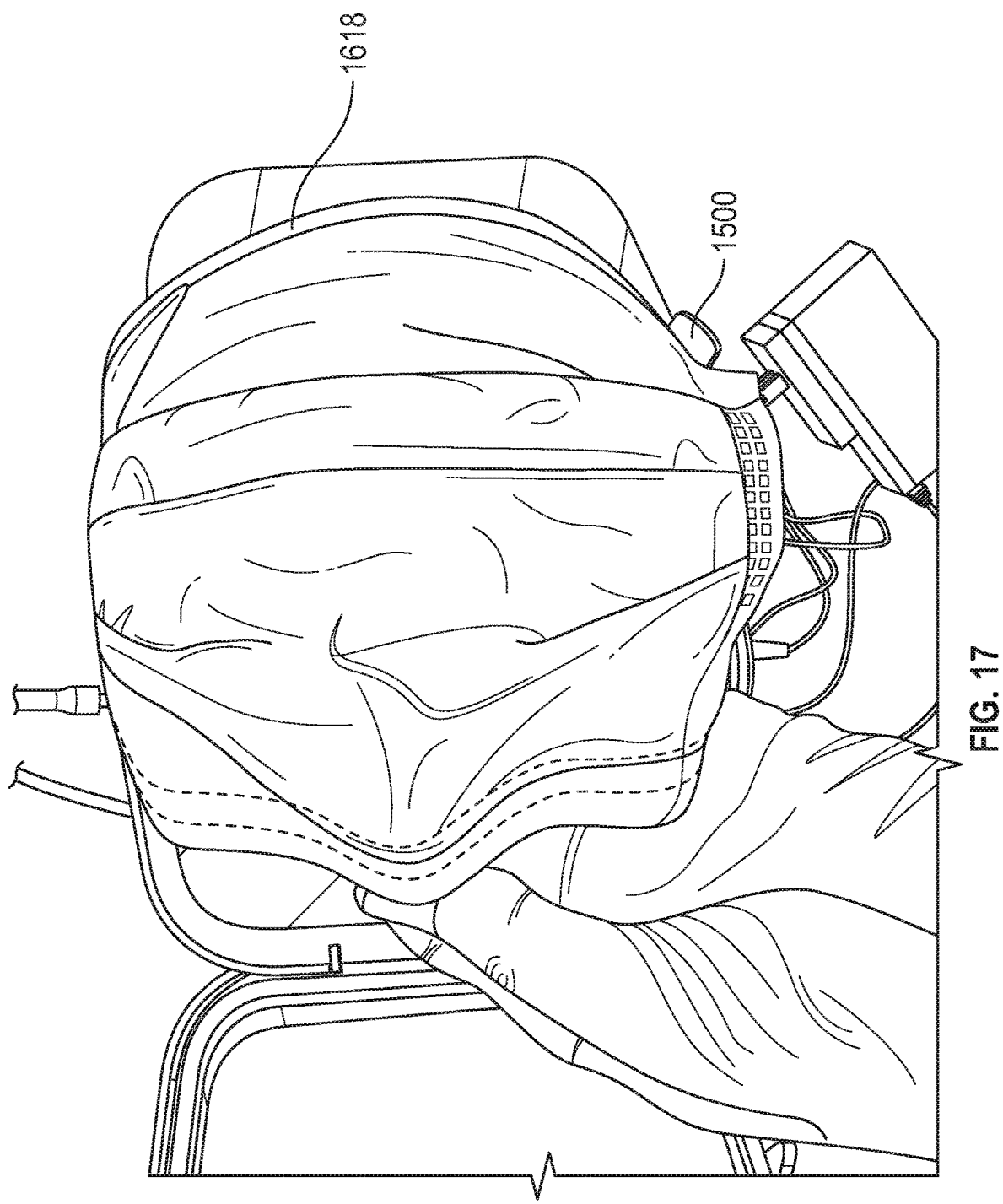
FIG. 17 shows a perspective top view of a mask on the adaptor of FIG. 15, consistent with embodiments of the present disclosure.

FIG. 17 shows a top perspective view of the mask 1618 coupled to the adaptor 1500.

While FIGS. 15-17 generally describe the fan 1501 as being coupled to the adaptor 1500. In some instances, the fan 1501 may be coupled to the sanitization device 1600 such that the adaptor 1500 can be positioned over the fan 1501.

While the adaptors disclosed herein are generally described as being separate from the sanitization device, in some instances, the adaptors may be integrally formed from a portion of the sanitization device.

An example of a sanitization device, consistent with the present disclosure, may include an ozone operating system configured to generate ozone, a sanitization compartment, a distribution line fluidly coupling the ozone operating system to the sanitization compartment, and an adaptor disposed within the sanitization compartment. The adaptor may be configured to couple to a mask and may be further configured to be fluidly coupled to the distribution line such that ozone passes through the adaptor and into the sanitization compartment.

In some instances, the adaptor may include an adaptor body having a mask supporting region and a base region. In some instances, the adaptor body may define an adaptor cavity. In some instances, the adaptor may further include an ozone distribution plate that separates the adaptor cavity into a first region and a second region, the distribution plate having a port configured to directly fluidly couple the distribution line to the second region. In some instances, the mask supporting region may include a plurality of apertures fluidly coupling the second region to the sanitization compartment. In some instances, a rib may extend between immediately adjacent apertures. In some instances, the rib may have an arcuate shape. In some instances, the apertures may have a triangular shape. In some instances, the adaptor may include a plurality of supports may extend from the base region. In some instances, the supports may be configured such that, when one or more elastic bands of the mask extend around the supports, the mask is coupled to the adaptor. In some instances, one or more sidewalls defining the sanitization compartment may include one or more passageways extending therethrough. In some instances, the one or more passageways may be configured to receive a connector that is fluidly coupled to the distribution line. In some instances, the sanitization device may further include a lid configured to extend across an open end of a cavity defined by the sanitization compartment, the lid being configured to sealingly engage a portion of the connector.

Another example of a sanitization device, consistent with the present disclosure, may include an ozone operating system configured to generate ozone, a sanitization compartment, a distribution line fluidly coupling the ozone operating system to the sanitization compartment, and an adaptor disposed within the sanitization compartment. The adaptor may be disposed within the sanitization compartment and configured to couple to a mask, the adaptor may include a fan and may be further configured to be fluidly coupled to the distribution line such that ozone passes through the adaptor and into the sanitization compartment.

In some instances, one or more sidewalls defining the sanitization compartment may include at least one of a first and a second passageway extending therethrough. In some instances, the first passageway may be configured to receive a connector that is fluidly coupled to the distribution line and the second passageway may be configured to receive a plug having one or more wires extending therethrough, the one or more wires being configured to electrically couple to the fan.

An example of an adaptor for a sanitization device, consistent with the present disclosure, may include an adaptor body and an ozone distribution plate. The adaptor body may define an adaptor cavity and the adaptor body may include a mask supporting region and a base region, wherein the mask supporting region includes a plurality of apertures extending through the adaptor body and into the adaptor cavity. The ozone distribution plate may separate the adaptor cavity into a first region and a second region.

In some instances, the ozone distribution plate may include a port configured to fluidly couple to a distribution line fluidly coupled to an ozone operating system. In some instances, immediately adjacent apertures may be separated by a rib. In some instances, the rib may have an arcuate shape. In some instances, the plurality of apertures may have a triangular shape. In some instances, a plurality of supports may extend from the base region. In some instances, the ozone distribution plate may be configured such that ozone gas flows from the second region through the apertures.

Another example of an adaptor for a sanitization device, consistent with the present disclosure, may include an adaptor body and a fan. The adaptor body may define an adaptor cavity and the adaptor body may include a mask supporting region and a base region, wherein the mask supporting region includes a plurality of apertures extending through the adaptor body and into the adaptor cavity. The fan may be disposed with the adaptor cavity.

In some instances, immediately adjacent apertures may be separated by a rib. In some instances, the rib may have an arcuate shape. In some instances, the plurality of apertures may have a triangular shape. In some instances, a plurality of supports may extend from the base region.

While the device to be sanitized is generally shown as being a mask herein, the device to be sanitized may be any device capable of being received within the sanitization device. For example, the device to be sanitized may be one or more keys, a wallet, a credit card, a mobile phone, a personal computer, a tablet, tools (e.g., screwdrivers, hammers, wrenches, and etc.), computer peripherals (e.g., mice, keyboards, and etc.), office supplies (e.g., staplers, binders, and etc.), reading materials (e.g., books, manuals, and etc.), dinnerware (e.g., cups, plates, silverware, and etc.), toiletries (e.g., toothbrushes, razors, and etc.), toys, baby supplies (e.g., bottles, teething rings, and etc.), and/or any other device capable of being received within the sanitization device. As may be appreciated, the device to be sanitized may be a unitary structure (e.g., a key) or may comprise multiple components (e.g., a mobile phone). Further, while the adaptors disclosed herein are generally described in the context of being configured to correspond to a mask, the adaptor may be configured to correspond to any device capable of being received within the sanitization device.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the claims.

What is claimed is:

1. A sanitization device comprising:
    an ozone operating system configured to generate ozone;
    a sanitization compartment;
    a distribution line fluidly coupling the ozone operating system to the sanitization compartment; and
    an adaptor disposed within the sanitization compartment and configured to couple to a mask, the adaptor being further configured to be fluidly coupled to the distribution line such that ozone passes through the adaptor and into the sanitization compartment;
    wherein:
        the adaptor includes an adaptor body having a mask supporting region and a base region;
        the adaptor body defines an adaptor cavity; and
        the adaptor further includes an ozone distribution plate that separates the adaptor cavity into a first region and a second region, the ozone distribution plate having a port configured to directly fluidly couple the distribution line to the second region.

2. The sanitization device of claim 1, wherein the ozone distribution plate is coupled to the adaptor body.

3. The sanitization device of claim 2, wherein the adaptor further comprises a plurality of supports extending from the base region.

4. The sanitization device of claim 3, wherein the plurality of supports are configured such that, when one or more elastic bands of the mask extend around the plurality of supports, the mask is coupled to the adaptor.

5. The sanitization device of claim 1, wherein the mask supporting region has a shape corresponding to an inward facing side of an air permeable mask, the inward facing side to face toward a user when the air permeable mask is worn by said user.

6. The sanitization device of claim 1, wherein the adaptor further comprises a fan.

7. The sanitization device of claim 6, wherein the ozone distribution plate comprises said fan.

8. The sanitization device of claim 1, wherein the mask supporting region includes a plurality of apertures fluidly coupling the second region to the sanitization compartment.

9. The sanitization device of claim 8, wherein a rib extends between immediately adjacent apertures of said plurality of apertures.

10. The sanitization device of claim 9, wherein the rib has an arcuate shape.

11. The sanitization device of claim 10, wherein each of the plurality of apertures has a triangular shape.

* * * * *